(12) United States Patent
Stuck et al.

(10) Patent No.: US 9,189,728 B2
(45) Date of Patent: *Nov. 17, 2015

(54) METHOD FOR THE AUTHENTICATION OF DOSAGE FORMS

(75) Inventors: Alexander Stuck, Wettingen (CH); Stefan Klocke, Karlsruhe (DE); Thomas Gering, Sarasota, FL (US); Harald Walter, Zurich (CH)

(73) Assignee: I-Property Holding Corp., Sarasota, FL (US)

( * ) Notice: Subject to any disclaimer, the term of this patent is extended or adjusted under 35 U.S.C. 154(b) by 579 days.

This patent is subject to a terminal disclaimer.

(21) Appl. No.: 13/010,510

(22) Filed: Jan. 20, 2011

(65) Prior Publication Data

US 2011/0186629 A1 Aug. 4, 2011

Related U.S. Application Data

(63) Continuation-in-part of application No. 12/841,649, filed on Jul. 22, 2010, now Pat. No. 8,626,672.

(60) Provisional application No. 61/227,826, filed on Jul. 23, 2009.

(51) Int. Cl.
*G06K 9/00* (2006.01)
*G06K 19/14* (2006.01)

(52) U.S. Cl.
CPC ............ *G06K 19/14* (2013.01); *G06K 9/00577* (2013.01)

(58) Field of Classification Search
None
See application file for complete search history.

(56) References Cited

U.S. PATENT DOCUMENTS

| | | | |
|---|---|---|---|
| 4,668,523 A | | 5/1987 | Begleiter |
| 5,502,944 A | * | 4/1996 | Kraft et al. ........................ 53/55 |
| 5,700,998 A | * | 12/1997 | Palti ............................... 235/375 |
| 5,845,264 A | * | 12/1998 | Nellhaus .......................... 705/28 |
| 5,992,742 A | | 11/1999 | Sullivan et al. |
| 6,505,461 B1 | * | 1/2003 | Yasunaga ......................... 53/562 |
| 6,543,692 B1 | * | 4/2003 | Nellhaus et al. .......... 235/462.01 |
| 6,608,717 B1 | * | 8/2003 | Medford et al. .............. 359/368 |
| 6,771,369 B2 | * | 8/2004 | Rzasa et al. .................... 356/326 |

(Continued)

FOREIGN PATENT DOCUMENTS

| | | |
|---|---|---|
| WO | 0110464 | 5/2001 |
| WO | 03005839 | 1/2003 |

(Continued)

OTHER PUBLICATIONS

European Patent Office, International Search Report, Form PCT/ISA/210 (3 pgs.), and Written Opinion, Form PCT/ISA/237 (5 pgs.), Apr. 1, 2011, for PCT/US2011/22065.

(Continued)

*Primary Examiner* — Jayesh A Patel
(74) *Attorney, Agent, or Firm* — Wood, Herron & Evans, LLP (57) ABSTRACT

The present invention relates to a method for the authentication of dosage forms such as tablets, in particular pharmaceutical tablets, by reading, i.e. detecting, code structure from the tablet, reading additional information from the package or on an information sheet, and then comparing the readings to verify authenticity. The code structure may be randomized on a plurality of tablets disposed in identifiable locations in a shared package such that the detected code structures define a unique digital signature for the package of tablets.

7 Claims, 6 Drawing Sheets

(56) References Cited

U.S. PATENT DOCUMENTS

| | | | |
|---|---|---|---|
| 6,776,341 B1* | 8/2004 | Sullivan et al. | 235/462.01 |
| 7,136,539 B2* | 11/2006 | Weyl | 382/280 |
| 7,185,812 B2* | 3/2007 | Wong et al. | 235/385 |
| 7,218,395 B2* | 5/2007 | Kaye et al. | 356/301 |
| 7,770,732 B2 | 8/2010 | Stroppolo et al. | |
| 7,815,117 B2* | 10/2010 | Tuschel et al. | 235/462.01 |
| 7,889,330 B2* | 2/2011 | Newcomb | 356/73 |
| 8,184,365 B2* | 5/2012 | Rolland et al. | 359/368 |
| 8,269,629 B2* | 9/2012 | Lyon et al. | 340/572.1 |
| 2005/0035138 A1* | 2/2005 | Guerra | 221/123 |
| 2005/0261937 A1 | 11/2005 | Silverbrook et al. | |
| 2006/0068006 A1 | 3/2006 | Begleiter | |
| 2006/0091208 A1* | 5/2006 | He et al. | 235/385 |
| 2006/0206714 A1 | 9/2006 | Gubo | |
| 2006/0226234 A1* | 10/2006 | Kettinger et al. | 235/487 |
| 2006/0255132 A1* | 11/2006 | Ortiz et al. | 235/383 |
| 2007/0086625 A1 | 4/2007 | Polli et al. | |
| 2007/0190133 A1 | 8/2007 | Bunick et al. | |
| 2007/0199991 A1 | 8/2007 | Haraszti et al. | |
| 2007/0219916 A1* | 9/2007 | Lucas | 705/58 |
| 2007/0241177 A1* | 10/2007 | Tuschel et al. | 235/375 |
| 2007/0286811 A1* | 12/2007 | Walter | 424/10.2 |
| 2008/0042843 A1 | 2/2008 | Kim | |
| 2008/0199406 A1* | 8/2008 | Walter et al. | 424/10.2 |
| 2009/0159174 A1* | 6/2009 | Grimard | 156/64 |
| 2010/0046825 A1* | 2/2010 | Haushalter | 382/141 |
| 2010/0110514 A1* | 5/2010 | Houha et al. | 359/2 |
| 2010/0143467 A1* | 6/2010 | Stuck et al. | 424/467 |
| 2010/0294844 A1* | 11/2010 | Loiret-Bernal et al. | 235/494 |
| 2010/0294927 A1* | 11/2010 | Nelson et al. | 250/307 |
| 2010/0297027 A1* | 11/2010 | Loiret-Bernal et al. | 424/10.2 |
| 2010/0297228 A1* | 11/2010 | Loiret-Bernal et al. | 424/467 |
| 2011/0026010 A1 | 2/2011 | Walker | |
| 2011/0091068 A1* | 4/2011 | Stuck et al. | 382/103 |

FOREIGN PATENT DOCUMENTS

| | | |
|---|---|---|
| WO | 2006047695 | 5/2006 |
| WO | 2007/137438 A1 | 12/2007 |

OTHER PUBLICATIONS

European Patent Office, International Search Report, Form PCT/ISA/210 (3 pgs.), and Written Opinion, Form PCT/ISA/237 (7 pgs.), Feb. 9, 2009, for WO 2009/051794 (also PCT/US2008/011868).

European Patent Office, International Search Report, Form PCT/ISA/210 (4 pgs.), and Written Opinion of the International Search Authority, Form PCT/ISA/237 (5 pgs.), Feb. 10, 2009, for WO 2009/051805 (also PCT/US2008/011889).

European Patent Office, International Search Report, Form PCT/ISA/210 (3 pgs.), and Written Opinion of the International Search Authority, Form PCT/ISA/237 (5 pgs.), Sep. 22, 2009, for WO 2010/011833 (also PCT/US09/51528).

The International Bureau of WIPO, International Preliminary Report on Patentability, Apr. 23, 2013, for counterpart International Patent Application No. PCT/2011/022065. (6 pages).

U.S. Patent and Trademark Office, International Search Report issued in International Patent Application No. PCT/US2009/51528, dated Sep. 22, 2009, (7 pages).

\* cited by examiner

METHOD FOR THE AUTHENTICATION OF DOSAGE FORMS

RELATED APPLICATION

This application claims priority to and is a continuation-in-part of U.S. Ser. No. 12/841,649, filed on Jul. 22, 2010, which claims priority to U.S. Ser. No. 61/227,826, filed Jul. 23, 2009. Each of these prior applications is incorporated herein by reference, in its entirety

FILED OF INVENTION

This invention relates to the tracking of pharmaceutical tablets, to verify authenticity.

BACKGROUND OF THE INVENTION

Pharmaceuticals and cosmetics are high technology products which require very specialized material systems and production procedures as well as very large investments in development and marketing. Because of public safety concerns, authorities place very stringent requirements on the verification and authenticity of such products. Companies therefore have to make huge investments in the tracking and tracing of these products to ensure authenticity. In addition, as these products usually have large sales margins and are distributed globally, it is not surprising that cosmetics manufacturers and pharmaceutical companies suffer from enormous losses due to counterfeiting. The problem has been aggravated by strongly increased sales over the internet, where everything from counterfeit Viagra to false glucose tests is readily available.

Track-and-trace features in the pharmaceutical market have been applied to packages. For example, holograms, optically variable inks, fluorescent dyes, and other identification features are attached to the packages, e.g., by adhesive tags. Alternatively, such labels are laminated to the carton or are directly applied to the packages. The main drawback of such labels is that they are not an integral part of the tablet and therefore do not provide 100% security. For example, if the authentic product is separated from the package, the package can be refilled with a false product. Therefore, direct verification of an authentic tablet, and ensuring that the authentic tablet is in the correct package, remains a primary concern.

Although there are some known approaches for secure labelling of the tablets themselves, each suffers from one or more drawbacks.

For instance, techniques based on forgery-resistant signatures, such as DNA of known sequence (U.S. Pat. No. 5,451,505) or molecules with characteristic isotopic composition or micro-particles with characteristic colour layer sequence (U.S. Pat. No. 6,455,157 B1), are considered unsuitable for pharmaceutical tablets, as these signatures are administered simultaneously and require additional regulatory approval.

WO2006/027688A1 describes an article, such as a tablet, having a visible diffractive microstructure on its surface or at an interface. Illuminated with white light, the tablet shows a rainbow colour effect similar to holograms. The diffractive microstructure can provide an indication of authenticity of the tablet. Although suitable for verification purposes, that document discloses a security element that is visible to the unaided eye. This visibility can tip off counterfeiters. Second, it is difficult to encode a large amount of data in such diffractive microstructures, and to do so consistently.

EP1958620A1 teaches a verification method based on three-dimensional structures such as barcodes or logos impressed or embossed in tablets, in particularly pharmaceutical tablets. Further methods to manufacture tablet compression tools are disclosed. This patent application is incorporated in its entirety.

A number of optical detection devices useful for analysing three-dimensional structures are known. White light interferometers are state of the art but operate rather slowly. Optical coherence tomography (OCT) is another known technique capable of visualising three dimensional patterns, even if they are located at an interface below the surface of an article. The depth that can be visualised in a material depends on the optical properties of the material. It can be up to a few millimeters at present. U.S. Pat. No. 6,469,489 describes an array sensor which is used for parallel optical low-coherence tomography (pOCT) which enables real-time 3D imaging for topographic pattern. It provides fast, three-dimensional and structural information with spatial resolution in the micrometer range. A plurality of electrical detection circuits with parallel outputs can form a one-dimensional or two-dimensional array sensor for the coherent or heterodyne analogue detection of intensity modulated optical signals simultaneously for all pixels with a high dynamic range. The array sensor may be used, e.g., for optical 3D measurements, and especially in optical low-coherence tomography. It is known to use OCT for investigating the human skin, to control the quality of fast production processes (e.g., in die-bonding), in SMD pick-and-place systems, as well as in mechanical inspection systems. Variants of these detection techniques do not use interferometry, but time-modulated optical signals to provide accurate 3D measurements of objects. Such variants often use parallel processing of lock-in signals on a single chip to provide fast and accurate distance information to an object. One example is time-of-flight (TOF) or related methods, where infrared or visible light from a camera's internal lighting source is time modulated and reflected by objects in the scene. It travels back to the camera, where its time of arrival is measured independently by each pixel on a sensor array or chip. In contrast to conventional cameras, such cameras provide a complete distance map of all objects in the field of view on a pixel-by-pixel basis.

BRIEF SUMMARY OF THE INVENTION

Altogether, there exists a need to verify the authenticity of tablets, in a manner that is contactless, fast, and reliable, and preferably also in a way that travels with the tablet.

Thus, it is an object of the present invention to mitigate at least some of the drawbacks of the state of the art relative to verifying the authenticity of tablets. In particular, it is an aim of the present invention to track and trace tablets through the production and supply chain, by marking the tablets themselves with a two- or three-dimensional code, for instance by embossing or impressing, and linking the code to information on the package or a package insert, in order to reduce false delivery. The two- or three-dimensional code essentially comprises tracking information that does not change the composition and the production process of the tablet, and that can easily be read. Further, it is an aim of the present invention to provide a fast, optical verification method for tablets and a system using that method to determine the authenticity of such tablets, while avoiding the drawbacks of known verification methods.

More particularly, the present invention relates to a track-and-trace method of tablets, namely pharmaceutical tablets wherein predetermined two- or three-dimensional code structures are formed in the tablets and are readable or detectable by a scanning device, for example by optical coherence tomography (OCT). These code structures are compared with information carrying structures or features on the package or on an information sheet placed in the package. Optionally, the information of the code structure is also compared with data in a database. One example of the code structures is provided in International Application No. PCT/US2009/51528, the disclosure of which is incorporated herein by reference, in its entirety.

The dimensional code structures may be visible or invisible to the human eye, but are detectable by the optical device in either case. The scanning device is configured to have a depth resolution of better than 5 microns and a lateral resolution of better than 10 microns. For example, the scanning device may use atomic force microscopy, environmental scanning electron microscopy, profilometers, time of flight sensing, reflection electron microscopy, optical interference microscope, or low voltage electron microscopy. The tablets may be coated with a contrasting agent to enhance detection of the dimensional code structures in some embodiments. Furthermore, the dimensional code structures of a plurality of pills disposed in identifiable positions in a package may create a unique digital signature for the package, which may be stored in a database for later association and verification of the package.

The present invention is described in more detail below. It is to be understood that the various embodiments, preferences and ranges are subject to a reasonable amount of variation and interchangeability. Further, depending on the specific embodiment, it is possible that one or more of the selected definitions, embodiments, or ranges that are described herein may not apply in certain circumstances.

Unless otherwise stated, the following definitions apply in this specification:

The terms "tablet" or "pill" are known in the field. They relate in particular to a single solid dosage form comprising at least one solid active ingredient and optionally solid excipients (such as binders and other components). Tablets are usually manufactured by compacting, e.g., pressing, powders or granules of the respective components. The term "active ingredient" ("a.i."), as used herein, is not limited to a "pharmaceutical active ingredient" but includes all kinds of ingredients that are active, such as flavours, fragrances, active ingredients for animal health, active ingredients for plant protection etc. Further, tablets may be coated, resulting in a tablet comprising a core and coating. Tablets are usually intended to be swallowed, or dissolved in water and are therefore of a suitable size and shape for the purposes of the disclosed invention.

An "element of authenticity" or "topography pattern" comprises one or more predetermined three-dimensional structures. Its presence proves authenticity of a tablet or pill. Suitable structures are for example 2- or 3-dimensional bar codes, such as data matrix or pharma code, logos, symbols and the like.

A "predetermined three-dimensional structure" denotes any structure detectable by an optical device that can be measured and produced with an accuracy of better than 50 microns, preferably better than 10 microns.

A "verification method" is a method, preferred an optical method, that allows distinguishing genuine articles, such as tablets or pills, from false articles.

Also, in the context of "reading" information or code, the specification also uses the word "detecting."

BRIEF DESCRIPTION OF THE DRAWINGS

The Figures embedded within this specification are intended to further illustrate the invention.

DETAILED DESCRIPTION OF THE INVENTION

Figure 1:
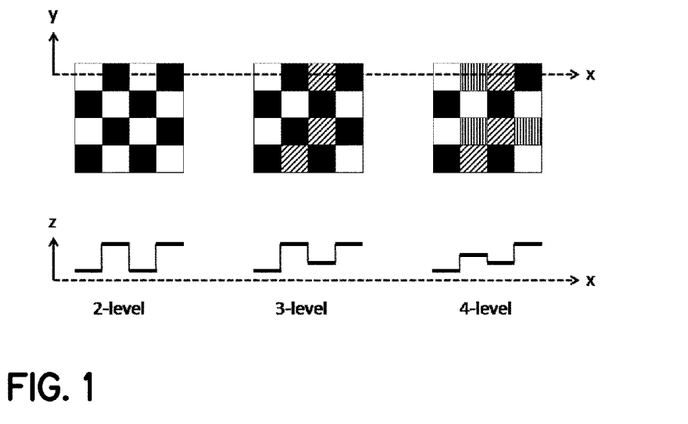
FIG. 1 shows a 4×4 matrix code with different depth levels.

FIG. 1 shows an example of a 4×4 matrix code with different depth levels. The x/y denotes the plane of the surface or interface of the tablet, and z is the perpendicular direction to this plane. 2-level: for example, normal black/white 2D bar code, 3-level: same code as 2-level code but additional third level contains a security code for authentication of the structure. 4-level: same as 2-level, but level 3 and 4 allow storage of additional product information on the same surface, like the 2-level code.

The invention relates to a track and trace method for tablets or a pills comprising at least one two- or -three-dimensional code structure on its surface or below a coating. Preferred the two- or -three-dimensional code structure is predetermined, wherein the smallest feature of the predetermined code structure is in the range of 10 μm up to 1 mm in lateral direction and between 1 μm and 1 mm in vertical direction. The whole code structure itself has typically a lateral dimension $1d_{code}$ of 50 μm×50 μm up to 10 mm×10 mm. The code structure shape is not necessarily square. Other shapes are possible as well. The code structure may carry information about the tablet, such as the name, the type of tablet, ingredients, date of production, etc. Suitable, preferred and especially preferred lateral and vertical structure sizes of the predetermined code structure are listed in table 1:

| | suitable range | preferred range | especially preferred range |
|---|---|---|---|
| $1d_{code}$ | 50 μm × 50 μm up to 10 mm × 10 mm | 500 μm × 500 μm up to 5 mm × 5 mm | 1000 μm × 1000 μm up to 2 mm × 2 mm |
| $s_{code}$ | 10 μm up to 1 mm | 30 μm up to 500 μm | 80 μm up to 300 μm |
| $h_{code}$ | 1 μm up to 1 mm | 2 μm up to 500 μm | 5 μm up to 50 μm |

In an advantageous embodiment, the optical detection device is capable of measuring 3D topologies. In this case the information of the code is built into the depth profile of the code structure as well as the lateral distribution of the code structure.

In a further advantageous embodiment, the optical detection device is an optical 3D camera which uses time-modulated optical signals to accurately measure depth, such as an optical coherence tomography, optical time of flight, or similar device.

The term tablet is known in the field and already defined above. Some tablets consist of nearly 100% active ingredient (a.i.). Aspirin is one such example. Typically, a tablet is a mixture of at least one active ingredient and excipients, usually in powder or granulated form, pressed into a solid dosage form. The mixtures consist of particles of different size, whereas the particle size distribution is considered critical for the compression process. A typical composition of such a powder mixture which is suitable for pharmaceutical tablets comprises 50-80% of a Lactose derivative (e.g. 73% Lactose Monohydrate), 10-50% of a cellulose derivative (e.g., 24% Microcrystalline Cellulose), 0.1-5% Silica, (e.g., 1% Aerosil (colloidal silica, anhydrous)), 0.1-5% of a fatty acid salt (e.g. 1% Magnesium-stearate) and 0.1-20% of a.i. (e.g., 1% a.i). Lactose and cellulose are the most widely used binding and filling agents, Aerosil improves the powder flow, and Mg-stearate is used as a lubricant. The particle size distribution of the powder is usually 15-25% smaller than 75 μm, 30-50% in the range of 75 μm-150 μm, 15-25% between 150 μm-250 μm, 5-15% between 250 μm-500 μm and less than 2% larger than 500 μm.

The tablet may comprise a pharmaceutically active ingredient ("pharmaceutical tablet" or "pill"). Pills are in particular subject to counterfeiting, and authentication devices are therefore of particular relevance.

The predetermined two- or three-dimensional code structure may be any structure and is not limited to any periodicity or particular shape. Suitable are for example, alphanumeric characters, geometric figures, bar codes, in particular pharma code and data matrix code, logos, or combinations thereof. The three-dimensional code structure may be either an impression or a ridge or both; preferred are impressed three-dimensional structures.

Preferably, the predetermined three-dimensional code structure is 50 μm to 5 mm in both lateral directions and 2 μm to 800 μm in vertical direction. These structures may possess two vertical levels or more (see FIG. 1). Structures of this size are detectable by an optical detection device and can be visible or invisible to the unaided eye. Such tablets are easy to manufacture, fully comply with existing manufacturing processes, and can be distinguished from false products, e.g., by a method as described below.

The two- or three dimensional code structures in the pill or tablet may be located in a macroscopic depression of the pill or tablet such as macroscopic letters or logos and the like. By doing so the structures are protected from being abraded by e.g. mechanical contacts of tablets during the production process or by de-powdering processes and the like. The code structures can be embossed or impressed in the cross of the logo of the company Bayer as it is used on Aspirin® tablets for instance.

In a first aspect, the invention relates to a verification and track-and-trace method for a tablet wherein the tablet comprises one or more two- or three-dimensional code structures on its surface or below a coating. The code structure is visible or invisible to the unaided eye. The method comprises detecting the code structure by an optical detection device and comparing the detected information, i.e., the code structure, with other information such as information which is encoded in information carrying structures or features on the package or on the information sheet in the package. Optionally, the information may also be compared to data saved in a database. The two- or three-dimensional code structure may be a predetermined structure. Alternatively, the two- or three-dimensional structure may be the structure obtained by a state-of the art manufacturing process for tablets, the fingerprint of the tablet pressing tool or tools. The information from the tablet is read by an optical verification device, preferably capable of measuring three-dimensional topologies with a depth resolution of better than 30 microns within less than 8 seconds and verified electronically. More particularly, the optical verification device may be capable of measuring three-dimensional topologies with a depth resolution of better than 5 microns and a lateral resolution of better than 10 microns.

In an advantageous embodiment, the data encoded in the code structure on the tablet or pill is read by the verification device through the package, for example through a blister or a glass tube. The package itself may contain embossed and/or printed additional code structures which are read by the same or a second device. The device then compares the code on the package with the code on the tablet and cross-verifies both with each other.

Figure 2:
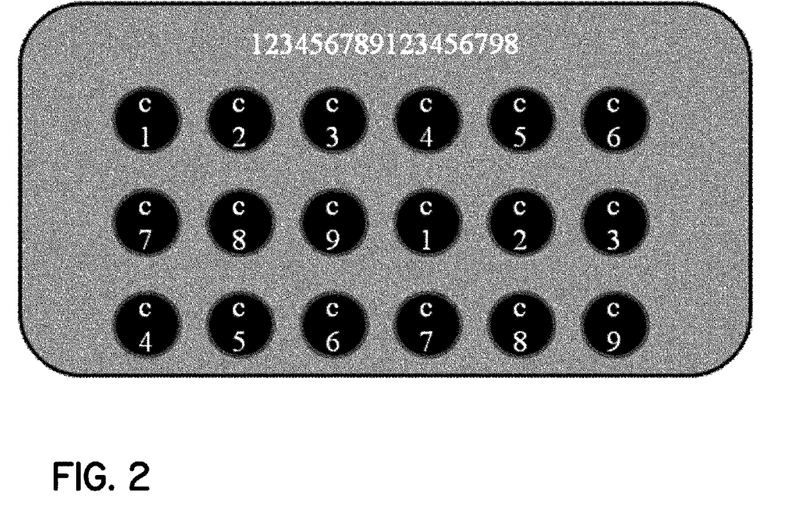
FIG. 2 shows an example of 18 tablets or pills packaged within a blister pack.

In still another embodiment at least two (or more) different code structures are present on tablets or pills within the same package. This can be realised easily by using in the production run tablet compressing tools with different code structures in the tool surface. If in a rotary press for example 64 compressing units are used and each of them manufactures tablets or pills with different code structures on average only every $64^{th}$ tablet or pill has the same code. If tablets or pills of such a production batch are packaged this inserts a degree of randomness in the package which can constitute a random code within itself. This random code generated by the geometrical arrangement of all tablets or pills in a package—for example within a blister—can be also read by the verification device and either be compared to a printed or embossed code on the blister or with a database for verification. FIG. 2 illustrates this based on an example with tablets with nine different code structures.

FIG. 2 shows an example of 18 tablets or pills packaged within a blister. Each tablet or pill contains a machine readable code c1-c9 (in this particular case). This code arrangement remains fixed in the supply chain and can be used for verification of the package. Each code c1-c9 on a pill can be different from the others or equal. The correct sequence of the security codes c1-c9 of this particular package might also be printed on the blister and used for cross verification of the package. Alternatively the pattern might be verified by comparison with an external database.

In an advantageous embodiment, the three-dimensional code structure contains a 1-, 2-, or 3-dimensional bar code, such as, but not limited to, a pharma or data matrix code. This code is read by an optical verification method as described above and compared to one or several additional data sets for verification. These additional data sets may also be, but do not have to be, on the pill or tablet or on the package of the pill. For example a step index code embossed into the pill with three or more distinguished height levels can contain several linked datasets; at most each level is a dataset of its own.

Figure 3A:
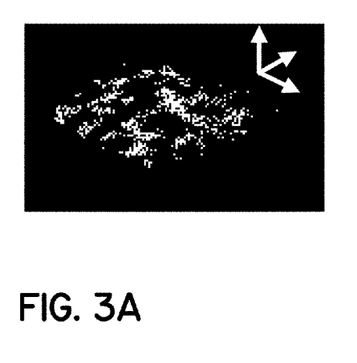
FIG. 3A shows a pOCT measurement of a datamatrix code impressed in the surface of a pharmaceutical tablet measured in air.
Figure 3B:
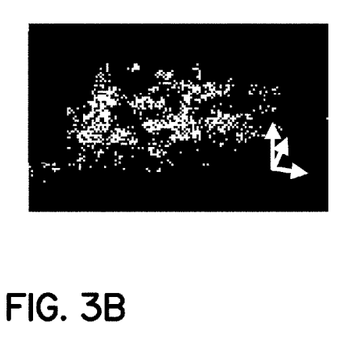
FIG. 3B shows a pOCT measurement of the datamatrix code of FIG. 3A measured through a plastic transparent blister pack.

In a further advantageous embodiment, the additional data set is printed and/or embossed in/on the package of the pill, such as a blister, box, bottle, etc. Alternatively a label comprising the data set is adhered to the package or it is applied by hot-transfer or lamination. The additional data set on the package is then compared with the data set from the pill or tablet to provide verification. For example, part of the data set on the pill contains a private cryptographic key that is used to unlock encrypted information on the additional data set on the package of the pill, or vice versa. In this way the system ensures that the pill actually is packed into the correct package, limiting the need to access external databases. To enhance security of the system, all data sets (on the package and on the pill) may be encrypted and be decrypted by the verification device before comparing and verifying the codes. In the case of a transparent and/or semitransparent package, such as a blister or bottle, this embodiment allows verification of the pill or tablet without opening the package (see FIG. 3). The method creates a direct link between the physical structure of the pill and information printed and/or embossed or otherwise marked on the package of the pill.

FIG. 3 shows a pOCT measurement of a datamatrix code of $1.6 \times 1.6 \: \mu m^2$ size impressed in the surface of a pharmaceutical tablet measured in air (a) and through a plastic transparent blister package (b). White denotes areas with impressed level in z-direction, while black denotes the surface of the tablet.

In a further advantageous embodiment, the additional data as well as encryption and description codes are stored in the verification device itself for verification.

Suitable optical detection devices are known in the field. In principle, any optical detection device capable of detecting three-dimensional structures as defined above is suitable. Preferred devices are selected from the class consisting of optical interferometry microscopes and time-modulated 3D cameras. They provide fast, three-dimensional and structural information with spatial resolution in the micrometer range. A plurality of electrical detection circuits with parallel outputs can form a one-dimensional or two-dimensional array sensor for the coherent or heterodyne analogue detection of intensity modulated optical signals simultaneously for all pixels with a high dynamic range. The array sensor may be used, e.g., for optical 3D measurements, and especially in optical low-coherence tomography. Variants of these detection techniques do not only use time domain interferometry, but other time-modulated optical signals to provide accurate 3D measurements of objects. Such variants often use parallel processing of lock-in signals on a chip to provide fast and accurate distance information to an object. One example is by time-of-flight (TOF) or related methods, where infrared or visible light from a camera's internal lighting source is time modulated and reflected by objects in the scene. It travels back to the camera, where its time of arrival is measured independently by each pixel on a sensor array or chip. In contrast to conventional cameras, such cameras provide a complete distance map of all objects in the field of view on a pixel-by-pixel basis.

A portable or fixed verification system may combine several of the above-mentioned 3D measuring systems as well as standard 2D camera systems to verify the embossed code simultaneously or in a fast time sequence on the pill and/or on the pill and the package of the pill.

As the described secure marking or information is also used for tracking and product tracing, a verification method is needed. Such method is preferably fast (i.e., it takes less than one second to distinguish forged from unique tablets and read the information on the tablet).

Figure 4A:
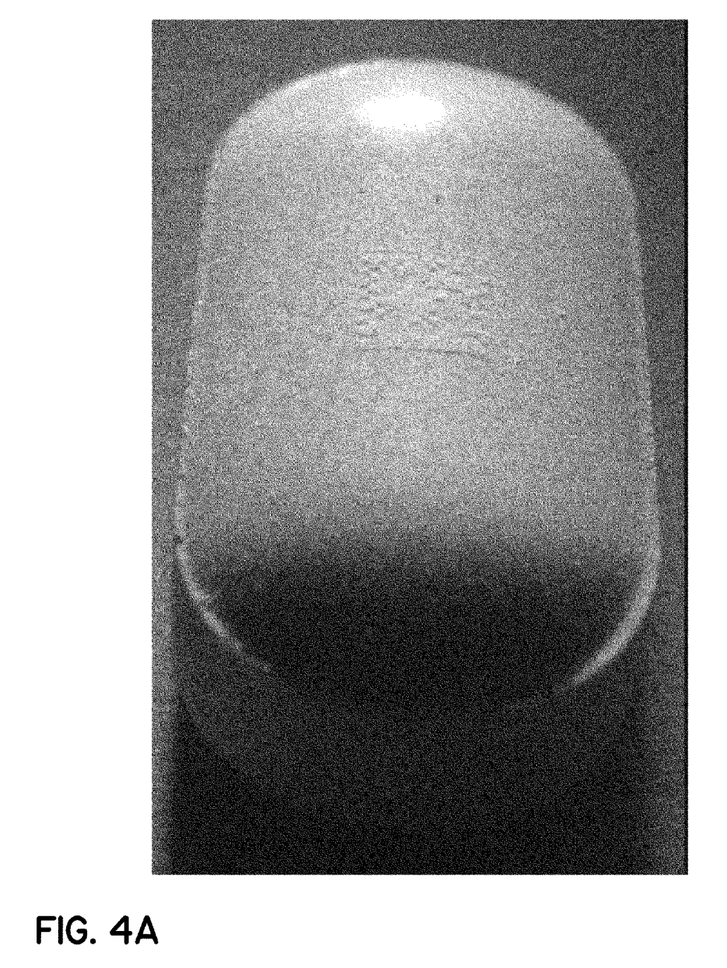
FIG. 4A shows an uncoated pill including an embossed datamatrix code.
Figure 4B:
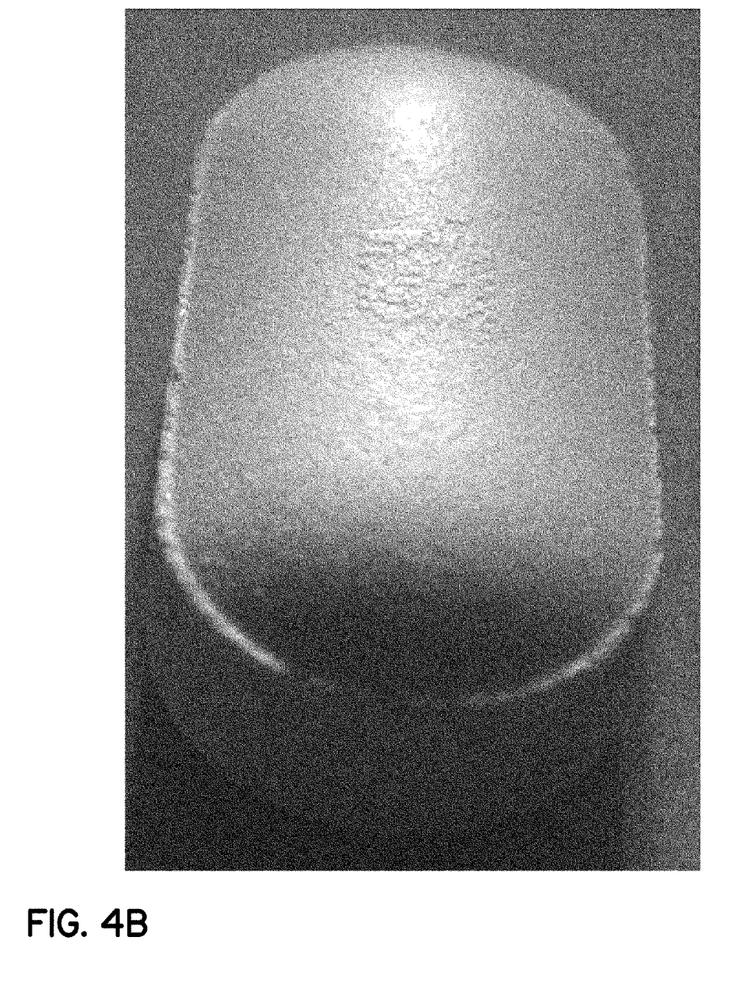
FIG. 4B shows a coated pill including an embossed datamatrix code where the datamatrix code is still visible to the naked eye.
Figure 4C:
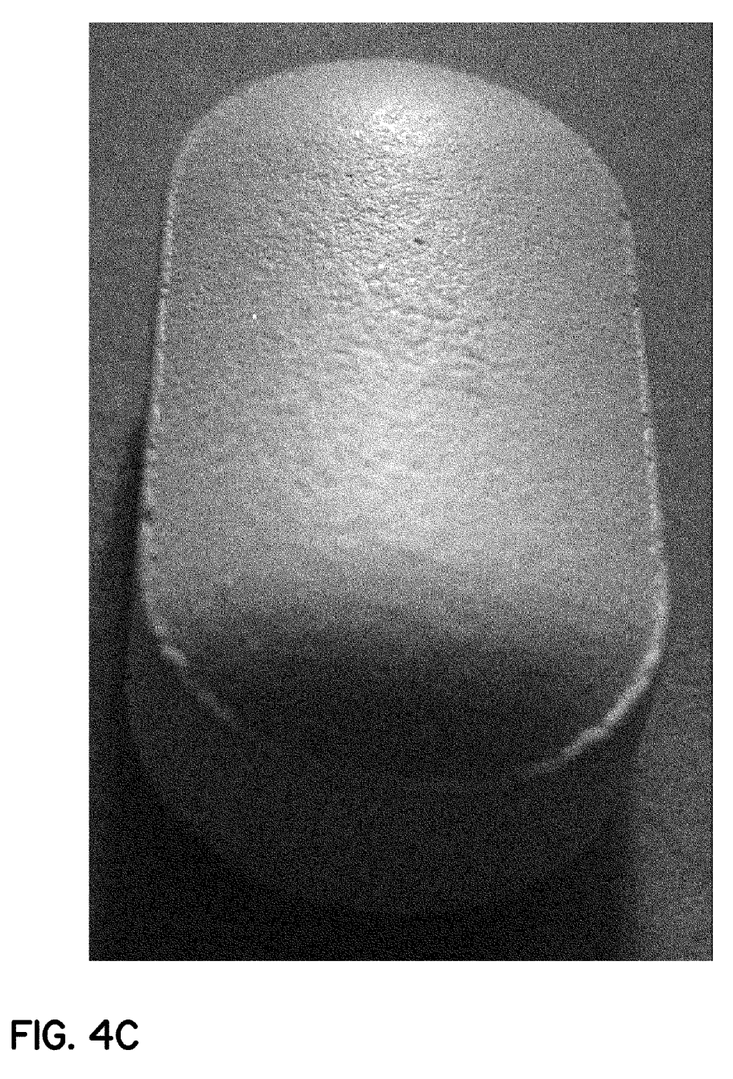
FIG. 4C shows a coated pill including an embossed datamatrix code where the datamatrix code is not visible to the naked eye.

In a further advantageous embodiment, the invention relates to a verification method as described above wherein said tablet comprises a core and a coating and wherein said predetermined structure is located at an interface between said core and said coating and wherein said method comprises the step of detecting said structure on the top surface of the coating. In this case the structure is such that the geometrical changes at the interface are conformally followed by the coating and still measurable at the coating surface. Depending on the structure used (overt or covert) it is visible or not visible by the naked human eye. To apply the verification method to a coated tablet is considered particularly useful as such tablets are predominant on the market. Also, the three-dimensional structure at the interface is protected against abrasion. In FIGS. 4A-4C such a tablet is shown with and without a coating. The predetermined code structure can be visible (overt) or not visible (covert) by the naked human eye.

FIG. 4A shows an uncoated pill containing an embossed datamatrix code. FIG. 4B shows the same pill with a coating applied. The datamatrix code is still visible by the naked eye and measurable. FIG. 4C shows a coated Pill with thicker coating. The datamatrix code is not visible but can be detected with appropriate measuring equipment.

In a further advantageous embodiment, the invention relates to a verification method as described herein wherein said tablet is located in a blister. In this embodiment, the verification of tablets takes place without unpacking them. Blisters are typical packages for tablets, in particular pharmaceutical tablets. Thus, spot tests at distributors or pharmacies and the like are possible.

In a further advantageous embodiment, the invention relates to a verification method as described herein wherein said tablet is located in a blister and said optical detection device is a OCT, especially a pOCT. As applicant has found OCT is a suitable detection method, as standard blister packages are transparent in the visible to NIR region (typically between 400 nm and 900 nm). Therefore even packaged tablets can be verified using OCT.

In a further advantageous embodiment, the invention relates to a verification method wherein said tablet comprises a core and a coating and wherein said predetermined structure is located at an interface between said core and said coating and wherein the step of detecting said structure on the top surface of the coating comprises the mechanical scanning of the surface. Applicant found that technologies useful for such mechanical scanning of a pill surfaces include but are not limited to an atomic force microscopes (AFM) or common profilometers. AFM technology is state-of-the-art and is described in the literature such as U.S. Pat. No. 5,144,833; Profilometers are also described in the literature, i.e., U.S. Pat. No. 7,619,190. Applicant chose the depth resolution of the measurement technique used so that it is better than 5 microns and the lateral resolution was chosen to be better than 10 microns. In this case the structure in the pill is such that the geometrical changes at the interface are conformally followed by the coating and still measurable at the coating surface. Depending on the individual structure chosen (overt or covert) it is visible or not visible by the naked human eye.

In a further advantageous embodiment, the invention relates to a verification method as described above wherein said tablet comprises a core and a coating and wherein said predetermined structure is located at an interface between said core and said coating and wherein said method comprises the step of detecting the random granular structure of the coating with said method, together with the predetermined structure either at the interface or at the surface. The measured size distribution of the granules of the coating provides a technology fingerprint, i.e., a verification that the correct coating material has been used, while the predetermined structure provides a verification of the tool used in production. Coupling together both subsets of information on the same pill provides a higher level of security. Typical coating granule sizes are in the range between 20 microns to 200 microns laterally. To facilitate identification of the predetermined structure, it is advantageous if the size distribution of the predetermined structure is distinctly different from the size distribution of the coating granules if the detection relies on the measurement of the top surface topology only. Technically this means that the spatial fourier transformation of the granules has peaks which do not strongly overlap the peaks in the spatial fourier spectrum of the predetermined structure.

Figure 5A:
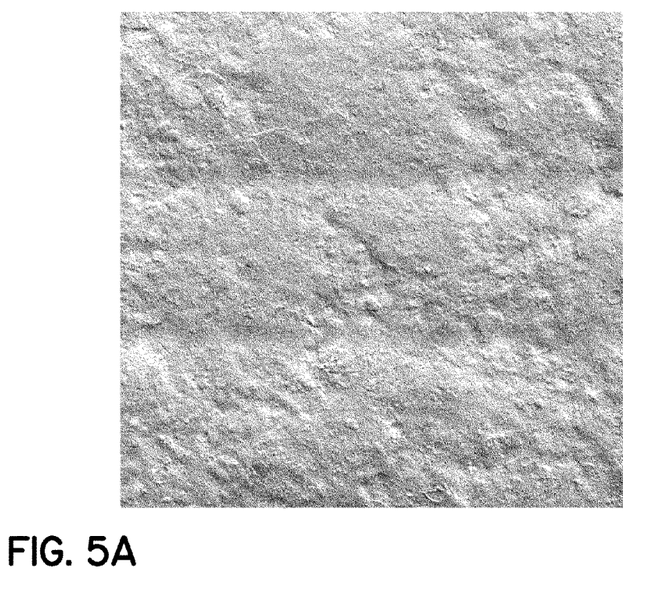
FIG. 5A shows an uncoated pill with a datamatrix code as measured by an environmental scanning electron microscope.
Figure 5B:
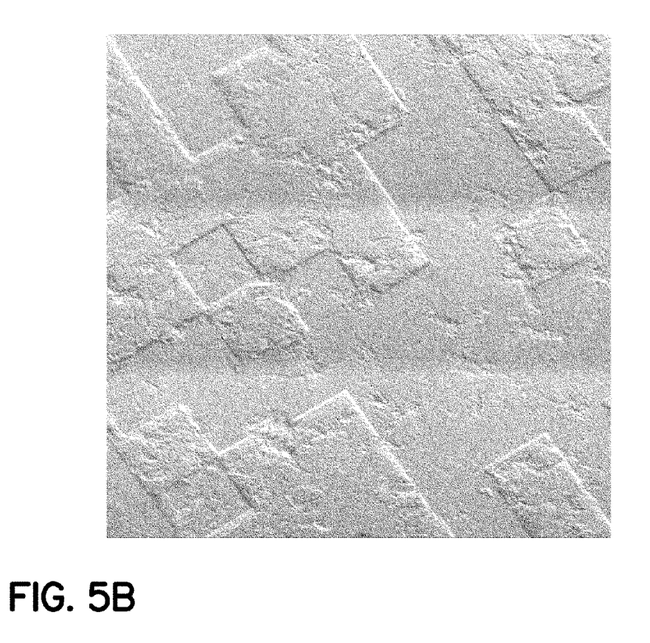
FIG. 5B shows a coated pill with a datamatrix code as measured by an environmental scanning electron microscope.

In a particular advantageous embodiment, the invention relies on a non-optical verification method, i.e., electron microscopy, to measure the code of a coated pill. Such a measurement is shown in FIGS. 5A and 5B. Applicant found that environmental scanning electron microscopes (ESEM) such as the solution described in U.S. Pat. No. 5,412,211 surprisingly allow the measurement of the surface of a pharmaceutical pill without any chemical alterations (such as coating with gold or similar metals). As shown in FIGS. 5A and 5B the contrast mechanisms of ESEM are such that the codes at the interface (and not only on the top surface of a coated pill) can be measured easily and clearly. The applicant also found that modern ESEM allow for fast and easy measurement of coded tablets. Measurement cycles are fast, i.e. they do not exceed 10 minutes of measurement time per sample and they do not require sample alterations, such as metallic coatings.

Applicant found that other embodiments of code measurements by use of electron microscopes require sample alterations, such as evaporation of thin metallic coatings on top of the surface. However, in principle such measurement methods can also be used for code verification. They include but are not limited to Reflection Electron Microscopy (REM), and Low Voltage Electron Microscopy (LVEM), REM is described in the literature, i.e. by J S Halliday and W Hirst in their article on "The examination of oxide films by REM", Proceedings of the Physical Society, Section B 68 178, 1955. One solution to LVEM technology is disclosed in U.S. Pat. No. 3,784,815.

FIG. 5A shows the surface of an uncoated pill with datamatrix code, measured with an environmental scanning electron microscope. FIG. 5B shows the same measurement but now with a coated pill. The datamatrix code at the pill interface is very well visible.

In a further advantageous embodiment, the invention relates to a verification method for a tablet (in particular a tablet as defined herein) comprising the step of analysing (detecting and recording) said tablet by means of optical interference microscopy (OIM—see U.S. Pat. No. 3,511,552 for reference) and comparing the obtained data set with a predefined data set. In this and other embodiments, the pill may be coated with a contrast-enhancing agent that improves the detection of the scanning device. In another embodiment, a sensor for detecting optical time of flight on a pixel-by-pixel basis as described above may also be used to detect and record the data on a tablet or package.

As the size of the powder particles of the tablet is predominantly in the range of 75 μm-500 μm the topography structure is superimposed on the grain structure of the particles.

Figure 6:
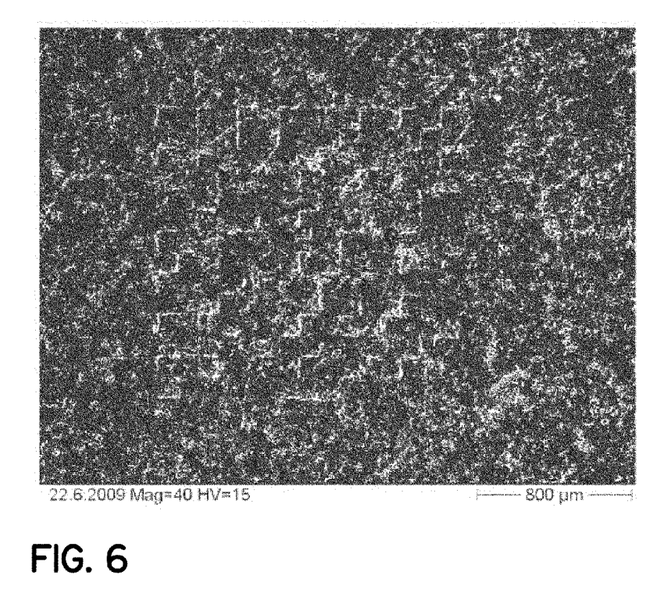
FIG. 6 shows a scanning electron microscopy picture of a pharmaceutical tablet with a datamatrix code structure impressed in the surface.

This has to be taken into account for the verification of the topography structure. FIG. 6 shows the grainy surface of a pharmaceutical tablet with a datamatrix code structure impressed in that surface. The picture was taken by scanning electron microscopy (SEM). The code structure can hardly be seen due to the grainy surface of the tablets.

FIG. 6 shows a scanning electron microscopy picture of a pharmaceutical tablet with a datamatrix code structure impressed in the surface. For the SEM image the tablet was coated with 50 nm gold in an evaporation chamber to render the surface conductive.

In still another embodiment the tablets or pills comprise one or more identical predetermined three-dimensional structures as defined above and these structures are located on both sides of the pill. This ensures a reliable method of verification, as at least one face of the tablet will be in the direction of the optical detection device. This is particularly suitable if tablets are verified through a blister package.

In a further embodiment the tablets or pills comprise two different predetermined three-dimensional structures as defined above on each side of the tablet or pill. This ensures a reliable method to verify the orientation of the tablet in the package. This is particular suitable if tablets are verified through a blister package. Methods to manufacture embossing or impressing tools for tablets or pills according to this invention are known in the art. Laser writing or e-beam lithography combined with dry etching are two possibilities. EP1958620A1 and WO2007144826A2 disclose another possibility based on photo lithography.

While this detailed description describes a number of preferred embodiments of the present invention, those skilled in the art will understand that these specific details are not to be read into the claims. The invention contemplates, and those skilled in the art will understand, that the various components and parameters described above are subject to a reasonable degree of variation or modification, without departing from the spirit and scope of the invention

We claim:

1. A method for tracking and tracing tablets or pills along a supply chain, each of the tablets or pills being provided with one of a plurality of different code structures, the method comprising:

detecting, by an optical or micro-mechanical scanning device provided at a location along the supply chain and that has a depth resolution of less than 5 microns and a lateral resolution of less than 10 microns, a first code signature of a selected package containing a plurality of the tablets or pills, the first code signature being a unique digital signature for the selected package that is defined by a correlated sequence of (1) the code structures on the plurality of the tablets or pills, which have been randomly placed at identifiable positions with respect to the selected package, and (2) the identifiable positions of the plurality of tablets or pills with respect to the selected package, and wherein the detecting of the first code signature further comprises:

detecting the different code structures provided on each of the plurality of tablets or pills in the selected package, wherein the different code structures of the tablets or pills are embossed into material defining an interior or exterior surface of the tablet or pill; and detecting the identifiable positions of each of the plurality of tablets or pills in the selected package; and correlating the different code structures detected with the identifiable positions to identify the correlated sequence defining the first code signature of the selected package;

detecting, by the scanning device, a second code signature provided on the selected package containing the plurality of tablets or pills, the second code signature including at least one code structure printed or embossed on the selected package and which is separate from the code structures defining the first code signature; and authenticating whether the selected package containing the plurality of tablets or pills is authentic solely by comparing the first and second code signatures that are detected by the scanning device to one another.

2. The method of claim 1 wherein the selected package is a blister pack.

3. The method of claim 1 wherein the different code structures formed on the plurality of tablets or pills are visible to an unaided human eye and therefore may be viewed without using a magnifier device or microscope.

4. The method of claim 1 wherein the different code structures formed on the plurality of tablets or pills are not visible to an unaided human eye and therefore must be detected with the scanning device or viewed with a magnifier device or microscope.

5. The method of claim 1 wherein the scanning device uses at least one of atomic force microscopy and environmental scanning electron microscopy.

6. The method of claim 1 wherein the tablet or pill is coated with at least one contrasting agent and wherein the scanning device uses at least one of time of flight sensing, reflection electron microscopy, optical interference microscopy, and low voltage electron microscopy.

7. The method of claim 1 wherein the scanning device uses parallel optical low-coherence tomography (pOCT) to perform the detecting steps.

* * * * *